(12) United States Patent
Grossman et al.

(10) Patent No.: US 8,685,374 B2
(45) Date of Patent: Apr. 1, 2014

(54) EDTA CONTAINING COMPOSITIONS AND USES THEREOF

(75) Inventors: Terry Grossman, Denver, CO (US); Raymond C. Kurzweil, Newton, MA (US)

(73) Assignee: Ray and Terry's Health Products, Inc., Wellesley Hills, MA (US)

( * ) Notice: Subject to any disclaimer, the term of this patent is extended or adjusted under 35 U.S.C. 154(b) by 3010 days.

(21) Appl. No.: 10/939,737

(22) Filed: Sep. 13, 2004

(65) Prior Publication Data

US 2005/0112200 A1    May 26, 2005

Related U.S. Application Data

(60) Provisional application No. 60/502,820, filed on Sep. 12, 2003.

(51) Int. Cl.
*A61K 8/00* (2006.01)

(52) U.S. Cl.
USPC .......................................................... 424/49

(58) Field of Classification Search
None
See application file for complete search history.

(56) References Cited

U.S. PATENT DOCUMENTS

| | | | | |
|---|---|---|---|---|
| 3,838,196 A | * | 9/1974 | Mercer et al. | 514/566 |
| 5,536,506 A | * | 7/1996 | Majeed et al. | 424/464 |
| 6,645,510 B1 | | 11/2003 | Coury et al. | |
| 2002/0169192 A1 | * | 11/2002 | Hayward et al. | 514/381 |
| 2004/0009896 A1 | * | 1/2004 | Glynn et al. | 514/6 |
| 2005/0261257 A1 | * | 11/2005 | Vermeer | 514/168 |

OTHER PUBLICATIONS

Efrain et al. (A text book on EDTA chelation therapy: A Retrospective study of 2,870 patients, 2001).*

* cited by examiner

*Primary Examiner* — Brian Gulledge
*Assistant Examiner* — Snigdha Maewall
(74) *Attorney, Agent, or Firm* — Fish & Richardson P.C.

(57) ABSTRACT

EDTA and EDTA related compositions and methods of using them are described herein. The compositions can have improved bioavailability over EDTA alone. The compositions can be useful in the treatment or prevention of atherosclerosis or for the treatment of heavy metal accumulation.

9 Claims, No Drawings

EDTA CONTAINING COMPOSITIONS AND USES THEREOF

CROSS-REFERENCE TO RELATED APPLICATIONS

This application claims priority under 35 USC §119(e) to U.S. Patent Application Ser. No. 60/502,820, filed on Sep. 12, 2003, the entire contents of which are hereby incorporated by reference.

TECHNICAL FIELD

This invention relates to EDTA containing compositions and therapeutic uses thereof.

BACKGROUND

Ethylenediamine tetra-acetic acid (EDTA) binds to metals, for example transition state metals, and is used therapeutically for the treatment of heavy metal accumulation. However, another potential therapeutic use for EDTA is treatment of atherosclerosis.

Atherosclerosis is a process where cholesterol, calcium and other minerals accumulate on the inside lining of blood vessels and, over time, clog them. This process, which is often associated with aging, is often referred to as hardening of the arteries, atherosclerosis and arterial plaque buildup. Atherosclerosis contributes to and accounts for the high numbers of individuals suffering from cardiovascular disease in the United States and other developed countries. Examples of such diseases are angina (chest pain due to poor blood circulation to the heart), heart attack, peripheral vascular disease (poor circulation to the legs and feet), and stroke. These conditions can be both physically disabling and mentally taxing to the patients. Moreover cardiovascular disease is the leading cause of death in the U.S.

EDTA can bind to metals deposited in the arterial wall and in plaques on the arterial walls of patients suffering from atherosclerosis. Intravenous EDTA is administered by some "complementary" physicians on an outpatient basis to treat atherosclerosis. However, the intravenous administration of EDTA is time consuming and expensive. A preferable method of treatment is one where the patient can administer the treatment himself, e.g. orally. While oral EDTA is available, its effectiveness has been limited by its poor absorption bioavailability.

SUMMARY

This invention is based in part on the use of agents in combination with EDTA that can improve the bioavailability, absorption, and/or half-life of EDTA in the body, thus improving the chances of successful oral administration of EDTA.

An aspect of the invention relates to novel EDTA-containing compositions, as well as methods of using the compositions. The compositions are useful in therapeutic applications, including modulation of disease or disease symptoms in a patient. The compositions are useful as metal chelators through their ability to bind metals, (e.g., transition state metals).

According to an aspect of the invention, an orally available composition including piperine and EDTA or a pharmaceutically acceptable derivative or pro-drug thereof is provided. In some instances, the composition also includes a pharmaceutical carrier or an additional therapeutic agent such as an ACE inhibitor, a calcium channel blocker, a beta-blocker, or a diuretic.

According to another aspect of the invention, an orally available composition including piperine and EDTA is provided.

According to another aspect of the invention, an orally available composition including enteric coated EDTA or a pharmaceutically acceptable derivative or pro-drug thereof is provided.

The enteric coating can include cellulose acetate phthalate or hydroxypropylmethylcellulose phthalate. The composition can also include a pharmaceutical carrier or an additional therapeutic agent such as an ACE inhibitor, a calcium channel blocker, a beta-blocker, or a diuretic. In some instances, the additional therapeutic agent is a statin. In some instances, the composition can also include piperine.

According to another aspect of the invention, an orally available composition including enteric coated EDTA is provided. The composition can also include piperine.

According to another aspect of the invention, a method for the treatment or prevention of atherosclerosis is provided. The method includes identifying a patient having atherosclerosis or at risk of having atherosclerosis, and orally administering to the patient a composition including EDTA or a pharmaceutically acceptable prodrug or derivative thereof and piperine. In some instances the EDTA is enteric coated. In some instances, the method also includes administering to the patient an additional therapeutic agent such as an ACE inhibitor, a calcium channel blocker, a beta-blocker, or a diuretic. The patient can be identified as having atherosclerosis or being at risk of having atherosclerosis using a calcium score (a measurement obtained by performing an ultrafast electron beam CT scan of the coronary arteries). In some instances the method may also reduce the calcium score.

According to another aspect of the invention, a method of the treatment or prevention of atherosclerosis is provided that includes identifying a patient having atherosclerosis or at risk for having atherosclerosis, and orally administering to the patient a composition including enteric coated EDTA or a pharmaceutically acceptable prodrug or derivative thereof. In some instances, the composition also includes piperine. In some instances, the method also includes administering to the patient an additional therapeutic agent such as an ACE inhibitor, a calcium channel blocker, a beta-blocker, or a diuretic. The patient can be identified as having atherosclerosis or being at risk of having atherosclerosis using a calcium score. In some instances, the method may reduce the calcium score of the patient.

Another aspect of the invention includes a method for the treatment of heavy metal accumulation. The method includes identifying a patient having heavy metal accumulation, and orally administering to the patient a composition comprising EDTA or a pharmaceutically acceptable prodrug or derivative thereof and piperine. The composition can be enteric coated. The composition can also be administered together with an additional therapeutic agent.

Another aspect of the invention includes a method of the treatment heavy metal accumulation, where the method includes identifying a patient having heavy metal accumulation, and orally administering to the patient a composition comprising enteric coated EDTA or a pharmaceutically acceptable prodrug or derivative thereof. In some instances, the composition also includes piperine. In some instances, the method also includes administering to the patient an additional therapeutic agent.

One or more advantages can be provided from the above. For example, a patient can administer EDTA compositions orally, and need not have them administered intravenously. Accordingly, a patient need not be admitted into a medical facility for treatment, which results in significantly lower costs of administration. In some instances, the compositions disclosed herein require less frequent administration than traditional orally administered EDTA. Moreover, where the EDTA is of a time release formulation, a patient can take higher dosages, as each dose is released in a controlled manner into the blood stream.

The details of one or more embodiments of the invention are set forth in the description below. Other features, objects, and advantages of the invention will be apparent from the description, and from the claims.

DETAILED DESCRIPTION

EDTA binds to metals in the body. Described below are techniques used in the use and preparation of orally available EDTA compositions in patients having atherosclerosis or heavy metal accumulation. The invention also relates to compositions including EDTA related compounds such as cyclohexyl EDTA monoanhydride (CDTAMA) as described in U.S. Pat. No. 5,021,571, or the EDTA related compounds described in U.S. Pat. No. 6,080,785 both of which are incorporated by reference in their entirety.

There are a variety of methods available to determine the efficacy of the administration of a composition described herein. If the EDTA containing composition is being used to treat heavy metal accumulation, the effectiveness of the composition can be determined, for example, using laboratory tests showing a decrease in amount of toxic heavy metals. On the other hand, if the EDTA containing composition is administered to a patient having coronary artery disease, the effectiveness of the compound can be determined, for example, by the patient's improved performance on a stress test, decrease in chest pain, or decrease in a patient's shortness of breath.

A possible alternative to monitor the effectiveness of a therapeutic agent in treating coronary artery disease includes the use of coronary artery calcium as a marker for calcified plaque (calcified deposits of cholesterol and fat buildup) in a blood vessel. Plaque formation is also known as atherosclerosis. The presence and amount of calcium detected in a coronary artery by an electron beam computerized tomography (EBCT) scan accurately reflects the presence and amount of calcified atherosclerotic plaque. Coronary artery calcium often occurs years or decades before the development of heart disease symptoms such as chest pain or shortness of breath. Electron beam computerized tomography is a very sensitive method of detecting this calcium, and is therefore a good screening test for coronary atherosclerosis.

The calcium score for each artery reflects the total amount of calcium in that specific artery of the heart. The total calcium score is equal to the total amount of coronary artery calcium in the heart. Because coronary artery calcium reflects the total amount of calcified plaque in the heart, the higher the calcium scores, the greater the amount of atherosclerosis in the heart. The calcium score does not correlate directly to the percentage narrowing of an artery, but it does correlate with the severity of the underlying coronary atherosclerosis (total plaque burden). However, the higher the calcium score in the heart, the greater the probability of a significant narrowing of arteries throughout the patient.

The calcium score is used to determine the calcium percentile, which compares the patient's calcium score to that of other asymptomatic or symptomatic people of the same age and sex. The calcium score, in combination with the calcium percentile, enables a physician to determine the risk to a patient of developing symptomatic coronary artery disease, and to measure the progression of disease and the effectiveness of treatment. Table 1 below provides an example of a correlation of calcium scores to risk of Coronary Artery Disease (CAD).

TABLE 1

Calcium Scores and correlation to CAD

| EBCT Calcium Score | Plaque Burden | Probability of Significant CAD |
|---|---|---|
| 0 | No identifiable plaque burden | Very low (generally <5% likelihood) |
| 0-10 | Minimal identifiable plaque burden | Very unlikely (generally <10% likelihood) |
| 11-100 | Definite (at least mild) | Mild or minimal coronary stenoses likely |
| 101-400 | Definite (at least moderate atherosclerotic plaque burden) | Nonobstructive CAD highly likely, although obstructive disease possible |
| >400 | Extensive | High likelihood (>90%) of at least one "significant" coronary stenosis |

Administering EDTA compositions to a patient may improve that patient's calcium score.

Disclosed are techniques for improving the effectiveness of EDTA administered orally. One approach combines EDTA with a bioavailability enhancer such as piperine. The resulting composition can improve absorption of the EDTA into the bloodstream, relative to the administration of EDTA alone. The combination of piperine with EDTA and EDTA related compounds could result in a higher plasma concentration and a longer presence of the EDTA in the body, thus improving the effectiveness of the EDTA or related compound. Accordingly, this can allow a smaller dose to be used (correlating to the increased effectiveness). The decrease in dose can correlate with decreased side effects (i.e., reduced toxicity) of the EDTA.

The effective bioenhancing dose of piperine for EDTA compounds can vary, however a dose of approximately 0.2-5% (wt/wt) (e.g., 0.25, 0.5, 1.0, 2.0, 4.0, 5.0% wt/wt or any range in between) of the active drug (e.g., EDTA) can be an appropriate bioenhancing dose of piperine to improve the bioavailability of the EDTA.

There are two plausible explanations of the role that piperine may have in improving the bioavailability of EDTA and related compounds: a) non-specific mechanisms promoting rapid absorption of drugs and nutrients, e.g., increased blood supply to the gastrointestinal tract, decreased hydrochloric acid secretion which prevents breakdown of some drugs, increased emulsifying content of the gut, increased enzymes like gamma-glutamyl transpeptidase which participate in active and passive transport of nutrients to the intestinal cells, and b) non-specific mechanisms inhibiting enzymes participating in biotransformation of drugs, preventing their inactivation and elimination.

The improved bioavailability with administration of piperine can be a result of both of the mechanisms, i.e., increased absorption from the gut and the slow down of biotransformation, inactivation and elimination from the system. The latter mechanism is probably the most important in sustaining the elevated blood levels of the EDTA, and making it more bioavailable to the tissue. Although a rapid absorption to the blood stream may account for increased blood levels of the EDTA, it is the inhibition of drug (i.e., EDTA) biotransforming enzymes with piperine that makes a drug stay in the body longer, in higher quantities, which makes it more effective.

EDTA and/or related compounds can also have an enteric coating to prevent degradation of the compound in the stomach. An enteric coating does not dissolve in the acidic environment of the stomach, but rather dissolves in the alkaline environment of the small intestine. Accordingly, the drug (e.g., EDTA or a related compound) is able to pass through the stomach and is released from the small intestine, which provides improved bioavailability. Methods of enteric coating are known to those of skill in the art as seen for example in C. Signorino, "Aqueous Enteric Coating," Pharm. Technol. Tableting & Granulation Yearbook 25-26 (1999) and M. P. Jordan et al, "A Comparison of the Performance Characteristics of Enteric Film Coating Systems," AAPS National Meeting (October 1999). Many examples of compounds used for enteric coating are known in the art, for example Eudragit-L-100 NF can be used as an enteric coating.

Another aspect of this formulation is that the EDTA is in a "time-release" formulation. One advantage of a time release formulation is that the time-release provides a more even amount of active drug (e.g., EDTA) in the blood stream over a prolonged period of time, thus reducing or in some instances avoiding the frequent peaks and valleys of medication levels one can encounter using more traditional methods of oral administration. Accordingly, the patient is provided with a more stable therapeutic environment. Another advantage of the time release formulation is that it allows the patient to take dosages of the EDTA or EDTA related compound with less frequency than would be required with uncoated EDTA. Examples of time release formulations include cocoa butter, waxes, polymers, etc. Another example of a time release formulation is methylcellulose K 100 M USP. Formulations that release the desired compound over about 6 to about 8 hours are generally preferred.

The term "bioavailability" refers to the degree and rate at which a substance (e.g., a drug) is absorbed into a living system or is made available at the site of physiological activity.

The term "diuretic" refers to a substance, which increases the production and elimination of urine.

The term "beta-blocker" refers to a pharmaceutical agent, such as propranolol, that opposes the excitatory effects of norepinephrine released from sympathetic nerve endings at beta-receptors and is used for the treatment of angina, hypertension, arrhythmia, and migraine. Also called beta-adrenergic blocking agent.

The term "ACE inhibitor" refers to an antihypertensive drug that blocks the formation of angiotensin in the kidney, leading to relaxation of the arteries and promotes the excretion of salt and water by inhibiting the activity of the angiotensin converting enzyme.

The term "calcium channel blocker" refers to a pharmaceutical agent that prevents or slows the influx of calcium ions into smooth muscle cells. Calcium channel blockers can be used, for example, to treat some forms of angina pectoris and some cardiac arrhythmias.

The term "statin" refers to of pharmaceutical agent that acts by competitively inhibiting 3-hydroxy-3-methylglutaryl coenzyme A (HMG CoA) reductase, an enzyme involved in the liver cholesterol synthesis.

A "pharmaceutically acceptable derivative or prodrug" means any pharmaceutically acceptable salt, ester, salt of an ester, or other derivative of a compound of this invention, which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention (e.g., EDTA and EDTA related compounds) may be modified by appending appropriate chemical functionalities (e.g., carboxylic acids, esters, amides, ethers, etc.) to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The methods herein contemplate administration of an effective amount of compound or compound composition to achieve the desired or stated effect. Typically, the compositions of this invention will be administered from about 1 to about 6 times per day. Each dose (i.e., administration) can be about 250-1500 mg EDTA or pharmaceutically acceptable derivative or prodrug thereof, (e.g., 100-750 mg., 150-600 mg., 200-400 mg., or about 250 mg). Such administration can be used as a chronic, acute, or prophylactic therapy. The amount of active ingredient that may be combined with the carrier materials to produce a single dosage form will vary depending upon the patient treated. A typical preparation will contain from about 5% to about 95% active compound (wt/wt) Alternatively, such preparations contain from about 20% to about 80% active compound.

Where EDTA or an EDTA related compound is administered together with piperine, the piperine is administered at about 0.2-5% (wt/wt) (e.g., 0.2-1.0, 1.0-2.5, or 2.5-5% wt/wt) relative to the EDTA or related compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a composition of this invention can be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Compositions of this invention can include EDTA or a pharmaceutically acceptable derivative or prodrug thereof; an additional agent including for example, piperine, acebutolol, bisoprolol, captopril, enalapril, hydrochlorothiazide, etc; and any pharmaceutically acceptable carrier, adjuvant or vehicle. Alternate compositions of this invention include EDTA or a pharmaceutically acceptable derivative or prodrug thereof; and a pharmaceutically acceptable carrier, adjuvant or vehicle. The compositions delineated herein include EDTA and derivatives thereof, as well as additional therapeutic agents if present, in amounts effective for achieving a modulation of disease or disease symptoms, including atherosclerosis or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention can be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

When the compositions of this invention include a combination of EDTA or a pharmaceutically acceptable prodrug or derivative thereof and one or more additional therapeutic or agents, both the compound and the additional agent should be present at dosage levels of between about 1 to 100%, and e.g., between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds, compositions, and methods of combination therapy delineated herein are useful to treat atherosclerosis and related symptoms. The concept of "treating" or "treatment" refers to activity that prevents, alleviates, or ameliorates any primary phenomena or secondary symptoms associated with atherosclerosis or heavy metal accumulation.

A number of embodiments of the invention have been described. Nevertheless, it will be understood that various modifications may be made without departing from the spirit and scope of the invention. Accordingly, other embodiments are within the scope of the following claims.

What is claimed is:

1. A method for the treatment of atherosclerosis, the method comprising;
    identifying a patient having atherosclerosis or at risk of having atherosclerosis, and
    orally administering to the patient a composition comprising EDTA or a pharmaceutically acceptable prodrug or derivative thereof and piperine; and
    administering to the patient an additional therapeutic agent, with the additional therapeutic agent being an ACE inhibitor.

2. The method of claim 1, wherein the EDTA is enteric coated.

3. The method of claim 1, wherein the patient is identified as having atherosclerosis or being at risk of having atherosclerosis using a calcium score.

4. The method of claim 3, further comprising determining a reduction in the calcium score of the patient.

5. A method for the treatment of atherosclerosis, the method comprising:
    identifying a patient having atherosclerosis or at risk for having atherosclerosis, and
    orally administering to the patient a composition comprising enteric coated EDTA or a pharmaceutically acceptable prodrug or derivative thereof; and
    administering to the patient an additional therapeutic agent with the additional therapeutic agent being an ACE inhibitor.

6. The method of claim 5, wherein the composition further comprises piperine.

7. The method of claim 5, wherein the additional therapeutic agent is a statin.

8. The method of claim 5, wherein the patient is identified as having atherosclerosis or being at risk of having atherosclerosis using a calcium score.

9. The method of claim 7, further comprising reducing the calcium score of the patient.

* * * * *